United States Patent [19]

Zeamer

[11] Patent Number: 4,870,838
[45] Date of Patent: Oct. 3, 1989

[54] CRYOSTAT

[76] Inventor: Geoffrey H. Zeamer, 583 Winter St., Holliston, Mass. 01746

[21] Appl. No.: 170,759

[22] Filed: Mar. 21, 1988

[51] Int. Cl.[4] ............................................. F25B 19/00
[52] U.S. Cl. .................................... 62/51.1; 62/50.7; 285/47; 285/904
[58] Field of Search .......................... 62/6, 514 R, 55; 285/47, DIG. 5

[56] References Cited

U.S. PATENT DOCUMENTS

| | | | |
|---|---|---|---|
| 3,466,886 | 9/1969 | Doose et al. | 62/55 |
| 4,462,419 | 7/1984 | Hensley | 62/514 R |
| 4,488,406 | 12/1984 | Eckels | 62/55 |
| 4,726,194 | 2/1988 | Mackay et al. | 62/55 |

*Primary Examiner*—Ronald C. Capossela

*Attorney, Agent, or Firm*—Fish & Richardson

[57] ABSTRACT

A cryostat for subjecting samples to extremely cold or extremely hot temperatures while simultaneously exposing them to a gas. The cryostat includes a temperature control assembly with a cryogen jacket-encased sample tube that defines a sample chamber. A heat exchanger is located at the base of the sample tube. The temperature control assembly further includes an exchange gas system for introducing gas into the base of the sample chamber. The cryostat includes a vacuum tail the temperature control assembly is inserted into. The vacuum tail comprises a vacuum jacket that surrounds the cryogen jacket and the sample base end that is integral with a manifold that is in communication with the sample chamber. Gas introduced into the sample chamber may be exhausted therefrom through the manifold.

9 Claims, 5 Drawing Sheets

CRYOSTAT

FIELD OF THE INVENTION

This invention relates generally to the field of cryostats, and more particularly to a cryostat able to cool and heat a sample placed therein through a wide range of temperatures while simultaneously exposing the sample to a gas.

BACKGROUND OF THE INVENTION

There is a need in industrial and scientific processes to cool samples to very low temperatures in order to obtain and/or observe their low temperature properties. This need has arisen in part because of the growing interest in superconductive materials, that is, materials that conduct electricity with minimal resistance to electric current flow. Typically, superconductivity is observed in certain materials that are cooled to 10° K., (−263° C.,) or below. The need to cool samples to extremely low temperatures is also growing because of the increasing desirability to observe and/or obtain other desirable properties, besides superconductivity, that are present in the samples when they are so cooled.

Currently, helium stage refrigerators and cryostats are used to cool samples to very low temperatures. Helium-stage refrigerators employ helium as a refrigerant to drain thermal energy from a sample so as to cool the sample. Typically, helium stage refrigerators operate by providing liquid helium in a closed-loop refrigeration system. The sample is exposed to the liquid helium, which extracts the thermal energy therefrom and converts the energy into the latent heat of evaporation so that the helium evaporates. The evaporation of the liquid helium produces gaseous helium that must be re-condensed, usually by a compression process, so that it can again function as a sink for the sample's thermal energy.

A cryostat includes a sample chamber in which samples are cooled. The cryostat includes a cryogen finger that extends into the sample chamber. A cold fluid, referred to as a cryogen, is circulated through the cryogen finger. The sample is cooled by the transfer of thermal energy from the sample to the cryogen. Heat absorbed by the cryogen causes it to either evaporate or expand so that it is exhausted from the cryogen finger. A recycling system, for example a compressor, is used to restore the cryogen to its original state so that it can again be pumped to the cryogen finger.

There are a number of limitations and disadvantages associated with the low temperature cooling systems currently available. Helium stage refrigerators have low heat exchange capabilities and consequently cool samples at a slow rate. Moreover, compression units, that are an integral part of helium-stage refrigerators, occupy a significant amount of space. There are difficulties associated with isolating samples in helium-stage refrigerators so that they are equally cooled over their entire surface area. Furthermore, the costs of providing the refrigerators, and the required compression units, is costly.

There are also limitations associated with currently available cryostats. Placing a sample in, and removing it from, a cryostat often requires a number of complicated steps. To date, it has been difficult to provide a cryostat that can be used with both liquid-state cryogen and gaseous-state cryogen. In other words, current cryostats typically are designed to be supplied with only a liquid cryogen, or only a gaseous cryogen. The utility of individual cryostats is thus limited because sometimes it is desirable to supply them with cryogen in a state that they cannot accept. These situations occur when there is a need to provide a specific type of cryogen in order to cool a sample to a specific temperature, or through a range of temperature, or when it would be desirable to provide a specific cryogen that requires only minimal auxiliary supply equipment and/or that can be provided with minimal expense.

Also, it is desirable in some instances to cyclically cool and heat a sample through a wide range of temperatures, for example from below 10° K. to above 700° K. (−263° C. to 430° C.). To date, it has provided difficult to provide a system that can be used cool and heat a sample through a cycle of very low temperatures, intermediate temperatures, and very high temperatures, and then repeat or reverse the cycle.

Furthermore, in order to perform some experiments with very cold samples, it is necessary to expose the samples to selected gases while simultaneously cooling or heating both the gas and the sample to a selected temperature that may be either extremely cold or hot. This procedure is performed in order to observe how the gas and the sample react together at a given temperature. Systems that can be used to heat samples and simultaneously expose them to a gas are known. However, to date, it has been very difficult to simultaneously cool a sample to a low temperature, and expose it to a gas.

SUMMARY OF THE INVENTION

This invention provides a new and improved cryostat for cooling and heating a sample through a wide range of temperatures while simultaneously exposing it to a gas.

In brief summary, the new cryostat of this invention comprises a temperature control assembly that is housed in a vacuum tail. The temperature control assembly includes a sample chamber for holding a sample. Surrounding the sample chamber is a cryogen jacket through which a cryogen circulates that cools the sample. A heat exchanger, located at the base of the sample chamber, provides a thermally conductive path between the sample and the cryogen jacket. A set of electrically energizable heating elements for heating the sample are embedded in the heat exchanger. An exchange gas system is provided for introducing a gas into the base of the sample chamber. The vacuum tail includes a vacuum jacket for insulating the temperature control assembly. Attached to the vacuum jacket is a gas manifold for receiving gas exhausted from the sample chamber.

A sample is initially placed in the sample chamber. To cool the sample, cryogen is circulated through the cryogen jacket to serve as a sink for the sample's thermal energy. The heating element may be activated to warm the sample above the normal low temperature the cryogen would otherwise cool it to. The sample may be heated by shutting off the flow of cryogen through the cryogen jacket and energizing the heating elements in the heat exchanger. The heat exchanger functions as a thermal energy source that heats the sample to the selected temperature.

While the sample is cooled or heated, it may be exposed to a gas introduced into the sample chamber through the exchange gas system. Gas introduced into the sample chamber is exhausted therefrom into the gas manifold.

The cryostat's readily cools and heats samples through a wide range of temperatures. The cryostat can thus be used to cool and heat a sample over a recyclable thermal curve over a wide range of temperatures.

The cryostat's exchange gas system provides a means for exposing a sample to a gas while both are at a very low temperature, a very high temperature, or a temperature therebetween. This makes it possible to expose a sample to an active gas in order to observe its reactions therewith while both are at a given temperature.

Alternatively, the exchange gas system can be used to expose a sample to an inert gas with selected thermal conduction characteristics. In such instances, the gas provide an enhanced thermal path between the exposed surfaces of the sample and the cryogen jacket and the heat exchanger and the cryogen jacket. The enhanced thermal path increases the overall thermal energy transfer efficiency from and to the sample. Consequently, the cooling and heating capabilities of the cryostat can be increased, and the sample can be cooled or heated to a substantially identical temperature over the whole of its surface.

The cryostat can be used with either a liquid state or a gaseous state cryogen. The cryostat can thus be used with almost any cryogen regardless of the cryogen's specific characteristics.

Another advantage of this cryostat is that the temperature control assembly and the vacuum tail can be readily disassembled and put back together. This makes it a relatively easy task to assemble the sample in the temperature control assembly at a first location, and then attach the temperature control assembly to the vacuum tail at second location so it can be subjected to the desired temperature cycle.

The cryostat is a compact unit and is very cost efficient to manufacture.

BRIEF DESCRIPTION OF THE DRAWINGS

This invention is pointed out with particularity in the claims. The above and further advantages of this invention may be better understood by referring to the following description taken in conjunction with the accompanying drawings, in which:

DETAILED DESCRIPTION OF AN ILLUSTRATIVE EMBODIMENT

Figure 1:
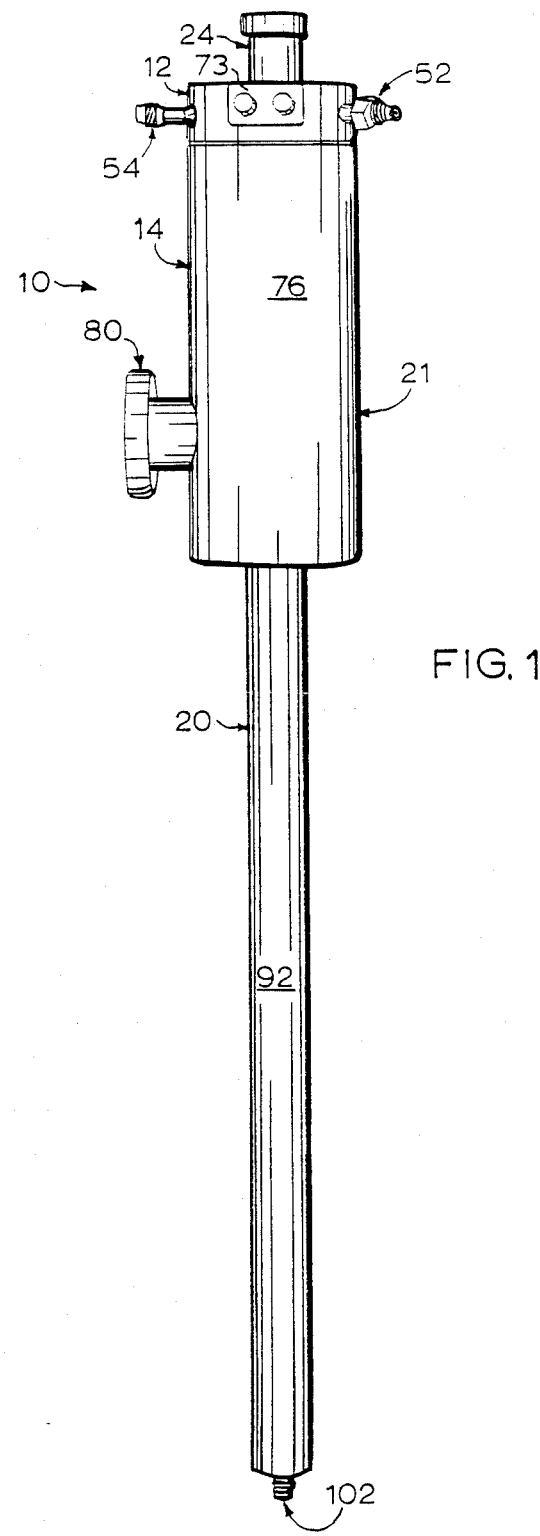
FIG. 1 is a side view of a cryostat constructed in accordance with this invention.
Figure 2:
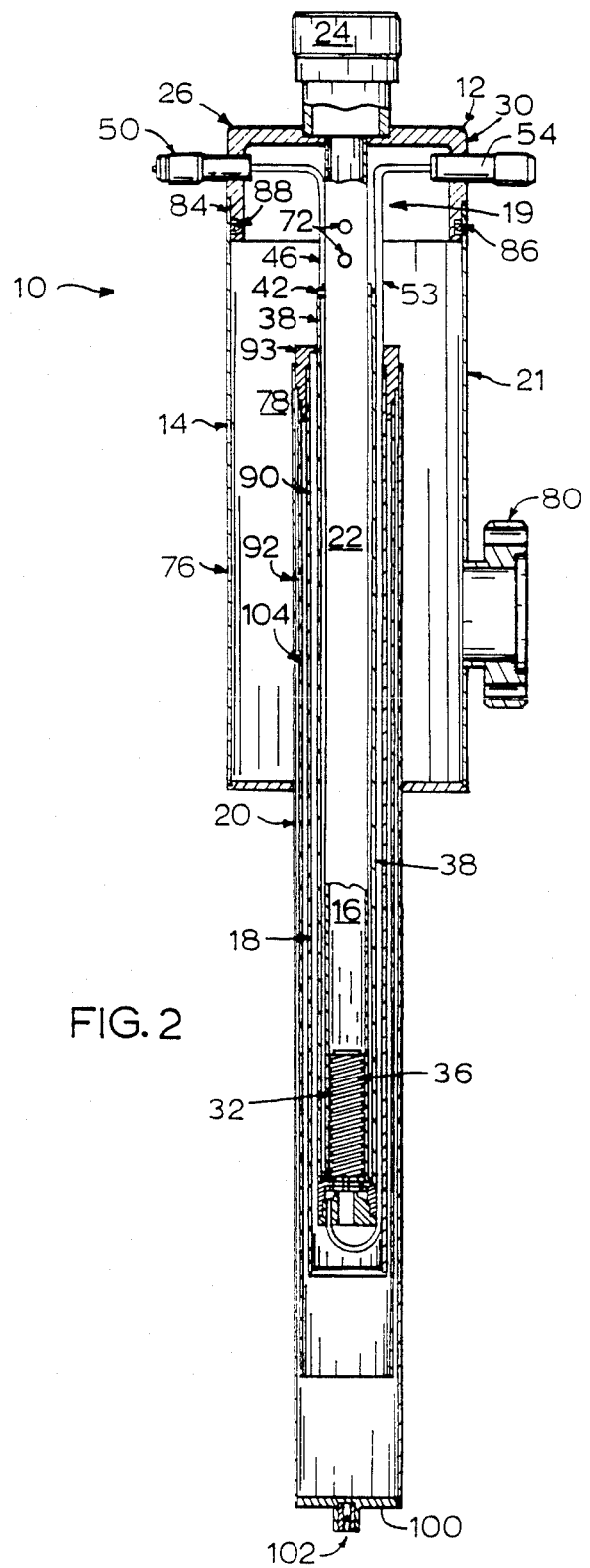
FIG. 2 is a cross-section view of the cryostat of FIG. 1 taken along line 2—2.
Figure 4:
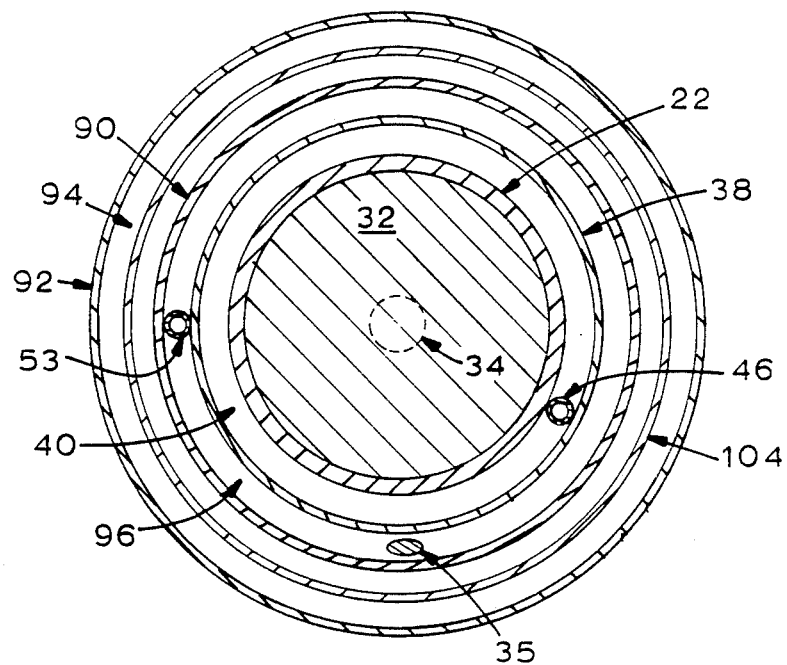
FIG. 4 is a cross-section view of the cryostat in FIG. 2 taken along line 4—4.
Figure 3:
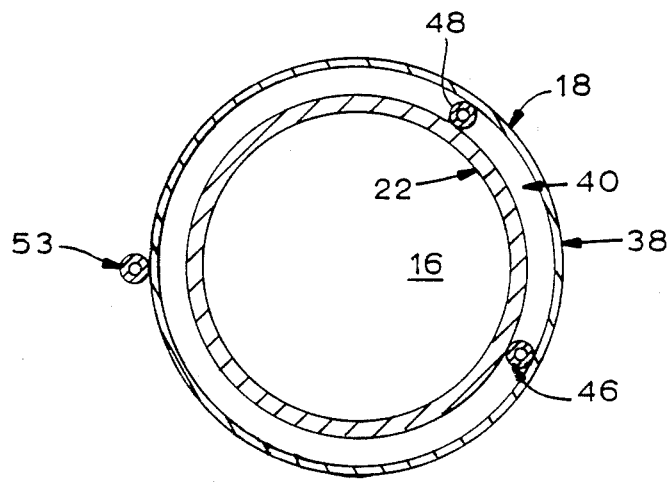
FIG. 3 is a cross-section view of the cryostat in FIG. 2 taken along line 3—3.
Figure 5:
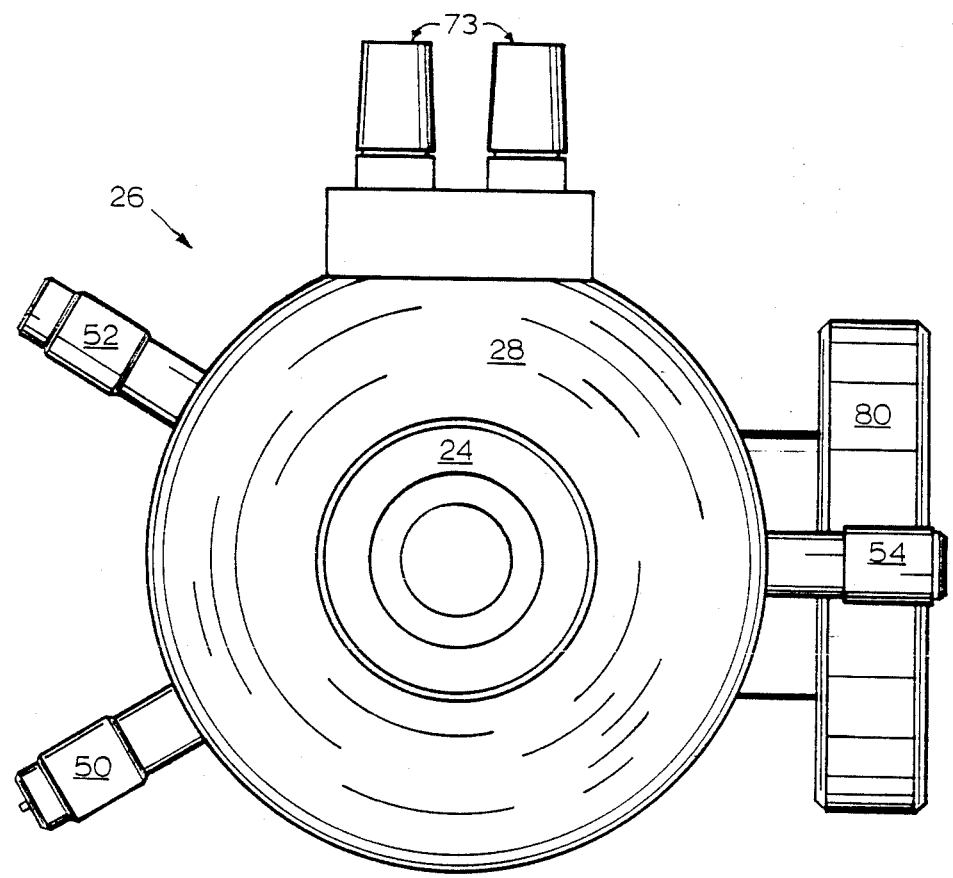
FIG. 5 is a top view of the cryostat of FIG. 1.
Figure 6:
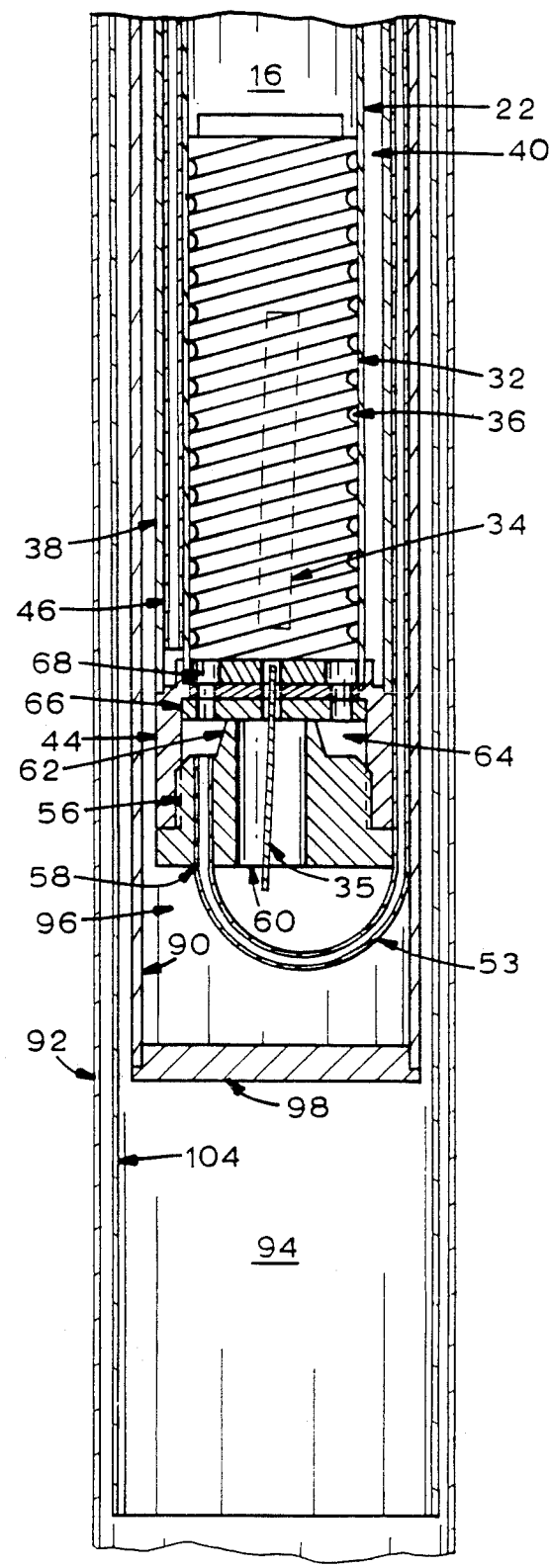
FIG. 6 is a enlarged cut-away view of the lower portion of the cryostat depicted in FIG. 2.

FIGS. 1 and 2 depict a cryostat 10 constructed according to this invention. The cryostat 10 includes a temperature control assembly 12 removably housed inside a vacuum tail 14. The temperature control assembly 12 includes a sample chamber 16 where sample to be cooled and heated to selected temperatures are placed. The sample chamber 16 is surrounded by a cryogen jacket 18 through which a cryogen circulates to cool the sample. The temperature control assembly 12 further includes an exchange gas system 19 through which gas can be introduced into the sample chamber 16 to expose the sample to the gas. The vacuum tail 14 includes an annular vacuum jacket 20 that surrounds and insulates the sample chamber 16 and temperature cryogen jacket 18. Attached to the vacuum jacket 20 is a gas manifold 21 through which gas, which has been introduced into the sample chamber 16 can be vented.

The temperature control assembly 12 is described in greater detail by reference to FIGS. 2 through 6. The temperature control assembly 12 includes an elongated sample tube 22, the interior of which defines the sample chamber 16. The sample tube 22 has an open top end to which a vacuum-sealable entrance fitting 24 is attached. The sample tube 22 and entrance fitting 24 are mounted to a temperature control assembly head 26 that includes a circular face plate 28 and a cylindrical outer wall 30, that depends from the face plate 28.

A heat exchanger 32, comprising a core of thermally conductive metal, is located at the bottom of the sample tube 22 and defines the base of the sample chamber 16. A set of electrically energizable heating elements 34 (shown in phantom) are located inside the heat exchanger 32. Conductors 35, thatextend out of the bottom of the heat exchanger 32, carry current to the heating elements 34. The heat exchanger 32 is dimensioned so that its outer wall is in physical contact with the inside wall of the sample tube 22. When a cryogen is circulated through the cryogen jacket 18, the heat exchanger 32 provides a thermal path from the sample chamber 16 to the cryogen jacket 18. When the heating elements 34 are energized, the heat exchanger 34 provides a thermal path from the heating elements 34 to the sample chamber 16. Formed along the length of the outer wall of the heat exchanger 32 are one or more grooves 36 so that gas from the exchange gas system 19 may be introduced into the sample chamber 16 by flowing therethrough. In one specific embodiment 10, the grooves 36 are formed in a helical pattern.

The cryogen jacket 18 includes the sample tube 22 and a cryogen shell 38 that surrounds it so as to define an annular cryogen space 40 therebetween through which the cryogen that cools the sample can circulate. The cryogen shell 38 extends from the base of the sample tube 22 upwardly to a location below the temperature control assembly head 26. A ring fitting 42 around the top of the sample tube 22 and an end piece 44 around the bottom end of the sample tube 22 secure the cryogen shell 38 in place. The ring fitting 42 and the end piece 44 are sealed fluid-tight to the sample tube 22 and the cryogen shell 38 by welding or other approriate means to prevent leaking from or to the cryogen space 40. Cryogen is introduced into the cryogen space 40 through a cryogen inlet line 46 that is attached to the outer wall of the sample tube 22 and has an opening in the base of the cryogen space 40 adjacent the bottom end of the heat exchanger 32. Cryogen is vented from the cryogen space 40 through a cryogen outlet line 48 also attached to the outer wall of the sample tube and that forms an inlet opening in the cryogen space immediately below the ring fitting 42. The cryogen inlet line 46 and cryogen outlet line 48 are respectively connected to a cryogen inlet coupling 50 and a cryogen outlet coupling 52 on the outer wall 30 of the temperature control assembly head 26. The cryogen inlet line 46 and cryogen outlet line 48 extend into the cryogen space 40 through separate openings formed in the ring fitting 42.

The exchange gas system 19 includes an exchange gas inlet line 53 through which gas from an external source is introduced into the sample chamber 16. The exchange gas inlet line 53 extends from an exchange gas inlet coupling 54 on the temperature control assembly head outer wall 30, is welded or otherwise secured along the outer wall of the cryogen shell 38, and opens into the bottom of the sample tube 22. The exchange gas inlet line 53 is formed with a U-shape bend adjacent the bottom end of the cryogen shell 38 and extends into a heat exchanger end piece 56 coupled into the end fitting 44 at the base of the sample tube 22. The end piece 56 forms a bore 58 offset from its axis into which the exchange gas inlet line 53 is inserted. The end piece 56 is further formed with an axial bore 60 which conductors 35 extend through. The heat exchanger end piece 56 has a stepped outer surface 62 so as to define annular space 64 between the end fitting 44 and the heat exchange end piece 56 gas from the exchange gas inlet line 53 enters.

A diffusion plate 66 is secured to the end fitting 44 above the heat exchanger end piece 55. The diffusion plate 66 is located in the bottom opening of the sample tube 22 so that the heat exchanger 32 rests on it. Formed in the diffusion plate 66 are a number of bores 68 located around its outer perimeter (two bores shown). The annular space 64 and the diffusion plate bores 68 are arranged so that when gas is discharged from the exchange gas inlet line 53, it will difuse through the space 64, pass through the bores 68 and flow through each of the heat exchanger grooves 36 at approximately the same rate. The diffusion plate 66 is also formed with a center bore 70 through which the conductors 35 extend. The heat exchanger end piece 56, the end fitting 44, the diffusion place 66, and the heat exchanger 32 are coupled together so that the only fluid communication from the exchange gas inlet is through the space 64 and diffusion plate bores 68 into the space defined by the heat exchanger grooves 36, and through the grooves 36 into the sample chamber 16. One or more gas openings 72, are formed in the sample tube 22 above the cryogen shell 28 through which gas introduced into the sample chamber 16 is vented.

The conductors 35 that supply current to the heating elements 34 extend from a set of terminals 73 on the temperature control assembly head outside wall 30. The conductors extend from the terminals 73, along the outside of the cryogen jacket 38 into the heat exchanger end piece 56. The conductors 35 are encased in an electrically and thermally insulating jacket so that any current flow therethrough does not effect cooling or heating of a sample by the cryostat 10.

The vacuum tail 14 includes the gas manifold 21 into which gas from the sample chamber 16 is vented. The gas manifold 21 includes a cylindrical manifold shell 76 that has an open end 77 the temperature control assembly head 26 is removably coupled to. The vacuum jacket 20 extends axially through the manifold shell 76 and is arranged so that approximately one-third of its total length is inside the manifold shell 76 and the remainder of its length extends outwardly therefrom below the closed end of the shell 76. The manifold shell 76 is dimensioned so that an annular manifold space 78 is defined between the inside wall manifold shell 78 and the outside wall of the vacuum jacket. Gas from the sample chamber 16 is vented into the manifold space through the sample tube openings 72. The gas manifold 74 has a coupling 80 that provides communication into the manifold space 78.

The temperature control assembly head 26 is provided with a gas tight coupling 82 to the gas manifold 74. The coupling 82 includes a stepped base surface 84 along the temperature control assembly head outer wall dimensioned to closely fit into the manifold shell 76. An O-ring 86 housed in a groove 88 formed in the stepped base surface 84 provides a gas-tight seal between the temperature control assembly head 26 and the manifold shell 76.

The vacuum jacket 20 surrounds the sample chamber 16 and cryogen jacket 18 so as to insulate the lower portion of the temperature control assembly 12. The vacuum jacket 20 includes an inner vacuum sleeve 90 contained within an outer vacuum sleeve 92, that are spaced apart so as to define a vacuum space 94 therebetween so that the sample chamber 16 and cryogen jacket 18 are thermally insulated. The outer vacuum sleeve 92 is welded to the closed bottom end of the manifold shell 76, and extends from a location below the top of the cryogen jacket 18 to a below the bottom of the temperature control assembly 12 so as to sufficiently insulate the temperature control against heat loss or gain through its base. The interior of the inner vacuum sleeve 90 defines an assembly space 96 dimensioned to house the sample chamber 16, the cryogen jacket 18, and the exchange gas inlet line 54 and the conductors 35 that are along the outside of the cryogen shell 38. The top end of inner vacuum sleeve 90 is sealingly secured to a spacer ring 93 attached to the top of the outer vacuum sleeve 92. The inner vacuum sleeve 90 terminates below the lowest point of the cryogen exchange gas inlet line 53 before it is looped into the heat exchanger and piece 56. An end plate 98 is sealingly attached to the open bottom end of the inner vacuum sleeve 90.

A bottom plate 100 is sealingly attached to the bottom end of the outer vacuum sleeve 92. A vacuum may be drawn on the vacuum space 94 through a normally closed vacuum 102 in the bottom plate 100. A cylindrical thermal radiation shield 104 is located in the vacuum space 94 between the inner vacuum sleeve 90 and the outer vacuum sleeve 92. The top end of radiation shield 104 is secured to the spacer ring 93. The radiation shield 104 blocks thermal radiation from unintentionally heating or cooling a sample in the cryostat 10.

When in use, the cryostat 10 is connected to an external cryogen supply-recirculating system (not-shown) through the cryogen inlet coupling 50 and outlet couplings 52, to an external electrical power source (not-shown) through the terminals 73, to an exchange gas supply system (not-shown) through the exchange gas inlet coupling 54, and to an exchange gas exhaust system (not-shown) through the manifold coupling 80. In addition, the cryostat 10 may be connected to an exchange gas recycling system (not-shown) that supplies gas to the exchange inlet coupling 54 and draws gas from the manifold coupling 80. Alternatively, the exchange gas inlet coupling 54 and the manifold 80 may be connected to a vacuum system (not-shown) that draws a vacuum on the sample chamber 16.

The cryostat 10 is used by positioning a sample to be cooled and/or heated in the sample chamber 16 proximate above, or on, the heat exchanger 32. The sample is positioned in the sample chamber by a dewar, a vacuum bottle, or other appropriate container. A temperature probe capable of monitoring extremely cold and extremely hot temperatures can be inserted in the sample chamber through the entrance fitting 24 and the fitting 24 is sealed gas-tight. The sample is cooled by circulating an appropriate cryogen, in either the liquid state or the gaseous state through the cryogen jacket 18. Cryogen is introduced into the cryogen space 40 through the cryogen inlet line 46 opening at the bottom of the cryogen space 40. This insures that the cryogen is well distributed throughout the cryogen space 40. The cryogen functions as a heat sink that drains thermal energy, that is, heat, from the sample, which can cool the sample to a temperature close to that of the cryogen. Cryogen that expands and/or evaporates as a consequence of absorbing the sample's thermal energy is vented back to the cryogen supply system through the cryogen outlet line 48.

The heating elements 34 may be energized while cryogen is cicrulated through the cryogens jacket 18. This makes it possible to cool the sample in the cryogen to a temperature that may be very cold, but is substantially above the normal cold temperature normally associated with the cryogen.

The sample may be heated by shutting off the flow of cryogen to the cryogen jacket 18 and activating the heating elements 34 in the heat exchanger 32. The energized heating elements function as a thermal energy source that heats the sample. Any residual cryogen that may be present in the cryogen space 40 that is vaporized as a consequence of the heat generated by the heating elements 34, and may be vented off through the cryogen outline 48. During both the cooling and the heating of the sample, the temperature probe inside the sample chamber can be used to monitor the temperature of the sample, and to control its cooling and heating.

The exchange gas system 19 allows a selected gas to be introduced into the sample chamber 16 to imerse the sample in the gas. Gas is introduced into the sample chamber 16 through the exchange gas inlet line 54. The gas exits the exchange gas inlet line 54, circulates through space 64 and passes through the diffusion plate bones 68 into the sample chamber 16. Initially, the gas in the sample chamber 16 flows through the grooves 36 in the heat exchanger 32, in which it is cooled if the sample is being cooled, or heated if the sample is being heated. The gas then flows into the sample chamber 16 above the 32 to surround the sample. The gas flows until it exits the sample chamber 16 through opening 72 into the manifold space 78. The gas may be vented from the manifold space 78 by an appropriate exhaust system (not shown) which may be attached to the manifold coupling 80.

It will be appreciated that different gases may be introduced into the sample chamber 16 to fulfill different objectives. In some situations, it may be desirable to introduce an inert, thermally conductive gas, such as helium, into the chamber. This type of gas increases the thermal conductivity between the exposed surface area of the sample, the cryogen jacket 18 and the heating elements 34 to enhance the cooling and heating capabilities of the cryostat 10. Depending on the sample, the cryogen used to cool the sample, and the exchange gas introduced into the sample chamber 16, the enhanced cooling and/or heating of the sample results in faster cooling and heating of the sample and/or the cooling and heating of the sample through an expanded range of temperatures. Moreover, the gas also provides a conductive path over almost the entire surface area of the gas so as to insure almost equal cooling and heating over the sample's surface area.

Alternatively, a reactive gas may be introduced into the sample chamber in order to observe reactions with the sample at selected temperatures over a broad temperature range. Depending on the specific composition of the gas it may be thermal conductive and thus enhance the heat extraction and heat delivery capabilities of the cryostat 10. When an active gas is introduced into the sample chamber 16, the exhaust system used to vent it may include analytical instruments to monitor changes in the gas that occur as a result of its reacting with the sample.

The exchange gas system 19 can also be used to cool and heat the sample in a vacuum by sealing the exchange gas inlet line 54 and attaching a vacuum pump to the manifold coupling 80 so that a vacuum is drawn on the manifold space 78 and sample chamber 16. When the sample chamber 16 is evacuated, it may be desirable to place the sample in direct physical contact with the heat exchanger 32 so as to insure thermal conductivity therebetween.

This cryostat 10 can be used to subject a sample, or a set of samples to recyclable temperature curves from 4° K to 770° K. (−269° C. to 500° C.) and back. The specific cooling and heating capabilities of a specific cryostat will depend on the sample being cooled, the cryogen used for cooling the sample, and the heat generating characterisics of the heating elements 34.

The cryostat 10 is not provided with a large amount of components that must be connected to directly to the cryostat 10 or located only a short distance away. Thus, the cryostat 10 can readily be used with test equipment the should be in close proiximity to the cryostat 10 so that they will properly function when used with the cryostat.

The temperature control assembly 12 can be disassembled and reassembled from the vacuum tail 14 by pulling the temperature control assembly head away from the manifold open face. This makes it possible to assemble the sample to be subjected to cooling and heating at a desirable location away from the vacuum tail 14 and the auxiliary equipment needed to run the cryostat 10, and then couple the temperature control assembly to the associated equipment when the cryostat is operated.

The foregoing detailed description has been limited to a specific embodiment of the invention. It will be apparent, however, that variations and modifications can be made to the invention with the attainment of some or all of the advantages of the invention. For example, it may sometimes be desirable to place a diffusion plate in the sample chamber 16 above the heat exchanger 32 to minimize the turbulence of the gas introduced into the chamber 16. Therefore, it is the object of the appended claims to cover all such variations and modifications as come within the true spirit and scope of the invention.

What is claimed as new and desired to be secured by Letters Patent of the United States is:

1. A cryostat comprising:
 (A) a temperature control assembly including;
   a sample tube defining a sample chamber therein, said sample tube having a selectively sealable open end and a closed base end distant from said open end;
   a cryogen jacket encasing a section of said sample tube including said base end, and spaced below said sample tube first end;
   and an exchange gas system including an exchange gas inlet line in communication with an opening formed in said sample tube base end, and said sample tube forming at least one vent opening above said cryogen jacket; and (B) a vacuum tail, housing said temperature control assembly, including;

a manifold shell defining a manifold shell open end said sample tube is inserted into, said manifold shell defining a manifold space in communication with said sample tube vent openings, a selectively sealable manifold coupling to said manifold space; and a vacuum jacket integral with said vacuum jacket including an outer vacuum sleeve, and an inner vacuum sleeve coaxial with and within said outer vacuum sleeve, said inner vacuum sleeve spaced apart from said outer vacuum sleeve so as to define a vacuum space therebetween, the interior of said inner vacuum sleeve defining a housing space for containing said cryogen jacket encased-sample tube base end therein; and (C) a coupling means for sealing attaching said sample tube to first end into said manifold shell open end.

2. The cryostat of claim 1 further including a heat exchanger in said sample tube based end, said heat exchanger having an outside wall dimensioned so as to be in physical contact with said sample tube, said heat exchanger outside wall forming at least one groove that extends the length of said heat exchanger outside wall.

3. The cryostat of claim 2 further including at least one selectively energizable heating element located within said heat exchanger.

4. The cryostat of claim 1 including a cryogen inlet line and a cryogen outlet line each of said cryogen lines connected to said cryogen jacket.

5. The cryostat of claim 1 including a cryogen shell extending axially over said sample tube and spaced apart therefrom so as to define a cryogen space therebetween.

6. The cryostat of claim 4 including a cryogen inlet line and a cryogen outlet line each of said cryogen lines in communication with said cryogen space.

7. The cryostat of claim 1 further including a temperature control assembly head coupled to said sample tube first end, couplings dimensioned to be coupled over said manifold shell open end, a means for sealing coupling said manifold shell and said temperature control assembly head.

8. The cryostat of claim 1 further including at least one selectively energizable heating element located within the base end of said sample tube.

9. The cryostat of claim 1 further including said exchange gas inlet line having an opening adapted to receive gas from an external source.

* * * * *